United States Patent
Choi et al.

(10) Patent No.: US 10,653,616 B2
(45) Date of Patent: May 19, 2020

(54) COMPOSITION FOR PREVENTING HAIR LOSS OR PROMOTING HAIR GROWTH, CONTAINING GINSENG-DERIVED EXOSOME-LIKE VESICLES

(71) Applicant: AMOREPACIFIC CORPORATION, Seoul (KR)

(72) Inventors: Eun-Jeong Choi, Yongin-si (KR); Yonghee Lee, Yongin-si (KR); Seung Hyun Shin, Yongin-si (KR); Kyeonghwan Hwang, Yongin-si (KR); Eun-Gyung Cho, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/760,882

(22) PCT Filed: Sep. 26, 2016

(86) PCT No.: PCT/KR2016/010747
§ 371 (c)(1),
(2) Date: Mar. 16, 2018

(87) PCT Pub. No.: WO2017/057881
PCT Pub. Date: Apr. 6, 2017

(65) Prior Publication Data
US 2018/0256488 A1   Sep. 13, 2018

(30) Foreign Application Priority Data

Sep. 30, 2015 (KR) .................. 10-2015-0137682

(51) Int. Cl.
*A61K 8/9789* (2017.01)
*A61Q 7/00* (2006.01)
*A61K 36/258* (2006.01)
*A61K 8/14* (2006.01)

(52) U.S. Cl.
CPC .............. *A61K 8/9789* (2017.08); *A61K 8/14* (2013.01); *A61K 36/258* (2013.01); *A61Q 7/00* (2013.01)

(58) Field of Classification Search
CPC ...... A61K 8/9789; A61K 36/258; A61K 8/14; A61Q 7/00
See application file for complete search history.

(56) References Cited

U.S. PATENT DOCUMENTS

2010/0104646 A1   4/2010   Kim

FOREIGN PATENT DOCUMENTS

| CN | 103054763 A | 4/2013 |
|---|---|---|
| CN | 103479682 A | 1/2014 |
| EP | 2255782 A1 | 12/2010 |
| IN | 201617003890 A | 7/2016 |
| JP | 2006036751 | * 2/2006 |
| JP | 2013-540150 A | 10/2013 |
| KR | 1020070052248 | * 5/2007 |
| KR | 10-2013-0039145 A | 4/2013 |
| KR | 10-1530490 B1 | 6/2015 |
| WO | 2012/053976 A1 | 4/2012 |
| WO | 2015/005700 A1 | 1/2015 |

OTHER PUBLICATIONS

Lee et al. KR 1020070052248, published: May 21, 2007, English machine translation obtained on Sep. 27, 2018.*
Lee, JP 2006036751, published: Feb. 9, 2006, english machine translation obtained on Aug. 1, 2019.*
Ju et al., "Grape Exosome-like Nanoparticles Induce Intestinal Stem Cells and Protect Mice from DSS-induced Colitis", Molecular Therapy, 21(7):1345-1357 (2013).
Marchant et al., "Membrane Systems Associated with the Plasmalemma of Plant Cells", Annals of Botany, 32(127):457-471 (1968).
Marchant et al., "The Ultrastructural Basis of Hyphal Growth", New Phytol., 66:623-629 (1967).
Ohno et al., "Roles of exosomes and microvesicles in disease pathogenesis", Advanced Drug Delivery Reviews, 65(3):398-401 (2013).
An et al., "Multivesicular bodies participate in a cell wall-associated defence response in barley leaves attacked by the pathogenic powdery mildew fungus", Cellular Microbiology, 8(6):1009-1019 (2006).
Halperin et al., "Ultrastructural Changes during Growth and Embryogenesis in Carrot Cell Cultures", J. Ultrastructure Research, 18:428-443 (1967).
Loyer et al., "Microvesicles as Cell-Cell Messengers in Cardiovascular Diseases", Circulation Research, 114(2):345-353 (Jan. 2014).
Regente et al., "Apoplastic exosome-like vesicles: A new way of protein secretion in plants?", Plant Signaling and Behavior, 7(5):544-546 (May 2012).
International Search Report from PCT/KR2016/010747 (dated Jan. 13, 2017).
Written Opinion from PCT/KR2016/010747 (dated Jan. 13, 2017).
Extended European Search Report from European Application No. 16852027.8, dated Mar. 13, 2019.
Office Action (NOtice of Reasons for Refusal) issued in related Japanese Application No. 2018-516485, dated Mar. 31, 2020.

(Continued)

*Primary Examiner* — Ali Soroush
*Assistant Examiner* — Genevieve S Alley
(74) *Attorney, Agent, or Firm* — Merchant & Gould P.C.

(57) ABSTRACT

Disclosed in the present specification are: a composition for preventing hair loss or promoting hair growth, containing *ginseng*-derived exosome-like vesicles; and a method for preparing the composition. The *ginseng*-derived exosome-like vesicles can have a diameter of 20-500 nm and can be isolated from *ginseng* root. The composition contains *ginseng*-derived exosome-like vesicles as active ingredients, thereby having an effect of inducing hair growth by activating dermal papilla cells (DPCs).

6 Claims, 6 Drawing Sheets

(56) References Cited

OTHER PUBLICATIONS

Jingyao Mu et al., "Interspecies communication between plant and mouse gut host cells through edible plant derived exosome-like nanoparticles," Molecular Nutrition & Food Research, 2014, vol. 58, No. 7, pp. 1561-1573.

Bow J. Tauro et al., "Comparison of ultracentrifugation, density gradient separation, and immunoaffinity capture methods for isolating human colon cancer cell line LIM1863-derived exosomes," Methods, 2012, vol. 56, pp. 293-304.

* cited by examiner

| Control | MNX 50 μM | Ginseng main ingredient 20ppm | Ginseng root exosome 10 μg/ml |
|---|---|---|---|
| 0.61 ± 0.05 | 0.86 ± 0.03 | 0.90 ± 0.01 | 0.78 ± 0.23 |

Hair shaft elongation (mm)

COMPOSITION FOR PREVENTING HAIR LOSS OR PROMOTING HAIR GROWTH, CONTAINING GINSENG-DERIVED EXOSOME-LIKE VESICLES

This application is a U.S. National Stage Application under 35 U.S.C. § 371 of International Patent Application No. PCT/KR2016/010747 filed Sep. 26, 2016, which claims the benefit of priority to Korean Patent Application No. 10-2015-0137682 filed Sep. 30, 2015, the disclosures of all of which are hereby incorporated by reference in their entireties. The International Application was published in Korean on Apr. 6, 2017 as WO 2017/057881.

TECHNICAL FIELD

The present specification discloses a composition for preventing hair loss or promoting hair growth, containing *ginseng*-derived exosome-like vesicles; and a method for preparing the composition.

BACKGROUND ART

Most animal cells have the ability to secrete intracellular origin extracellular vesicles having various sizes and components, and these extracellular vesicles are found in all biological fluids including blood, urine, saliva, and cell culture fluids (Loyer X, Vion A C, Tedgui A, Boulanger C M. Microvesicles as cell-cell messengers in cardiovascular diseases. Circ Res 2014; 114:345-53) (Ohno S, Ishikawa A, Kuroda M. Roles of exosomes and microvesicles in disease pathogenesis. Adv Drug Deliv Rev 2013; 65:398-401).

Extracellular vesicles are membrane-structured vesicles having a size of about 20 nm to about 5 μm in diameter, are heterogeneous in size and composition, and include a number of different species such as exosomes (about 30 to 100 nm), ectosomes, microvesicles (about 100 to 1000 nm), and microparticles.

The different types of extracellular vesicles are distinguished from one another based on their origin, diameter, density in sucrose, shape, sedimentation velocity, lipid composition, protein marker, or secretion mode (i.e., whether it is signal (inducible) secretion or spontaneous (constitutive) secretion). For example, microvesicles are known to be a membrane vesicle having an irregular shape of about from 100 to 1,000 nm, to bud toward the outside of the plasma membrane (originated from the plasma membrane), and to have integrin, selectin, a marker including a CD40 ligand, and lipids including phosphatidylserine. Meanwhile, exosomes are known to be the smallest membrane vesicles having a cup shape of about from 30 to 100 nm (<200 nm), to bud from the inside of late endosomes (originated from endosomes), and to have tetraspanins of CD63 and CD9, markers including TSG101 and ESCRT, and lipids including cholesterol, sphingomyelin, ceramide, and phosphatidylserine.

Extracellular vesicles reflect the state of the origin cells (donor cells) from which the extracellular vesicles are secreted, exhibit various biological activities depending on the cells from which the extracellular vesicles are secreted, and play an important role in cell-cell interactions by transporting genetic materials and proteins between cells.

In plants as well, the fusion of the plasma membrane and the multivesicular bodies causes the release of microvesicles into the extracellular space and vesicles in the multivesicular bodies are observed in the extracellular space in various plant cells of various plant species (Marchant R, Peat A, Banbury G H. The ultrastructural basis of hyphal growth. New Phytol. 1967; 66:623-629) (Halperin W, Jensen W A. Ultrastructural changes during growth and embryogenesis in carrot cell cultures. J Ultrastruct Res. 1967; 18:428-443) (Marchant R, Robards A W. Membrane systems associated with the plasmalemma of plant cells. Ann Bot. 1968; 32:457-471). In addition, it has been reported in recent studies that exosome-like nanoparticles derived from plant cells are similar to exosomes derived from mammalian cells in nano-sized vesicle structures and nanoparticle compositions (An, Q, Hückelhoven, R, Kogel, K H and van Bel, A J (2006). Multivesicular bodies participate in a cell wall-associated defence response in barley leaves attacked by the pathogenic powdery mildew fungus. Cell Microbiol 8: 1009-1019) (Regente, M, Pinedo, M, Elizalde, M and de la Canal, L (2012). Apoplastic exosomelike vesicles: a new way of protein secretion in plants? Plant Signal Behav 7: 544-546).

Hitherto, exosomes have been used primarily as biomarkers and techniques to utilize the efficacy of exosome itself and thus to use the exosome in specific applications have not yet been developed. In particular, specific applications of membrane-structured exosome-like vesicles derived from plant cells have been little known, and in the case of *ginseng*, the hair growth effect of *ginseng*-derived extract or a single component thereof has been reported but the hair growth effect of membrane-structured exosome-like vesicles, which is a complex physiologically active substance extracted from *ginseng*, has not been reported. Prior art relating to compositions for preventing hair loss and promoting hair growth is disclosed in Korean Patent No. 10-1530490.

SUMMARY OF INVENTION

Technical Problem

In an aspect, an object of the present specification is to provide a composition for preventing hair loss or promoting hair growth, containing an exosome-like vesicle, which is a complex physiologically active substance derived from *ginseng*, as an active ingredient.

In another aspect, an object of the present specification is to provide a method for preparing the composition.

Solution to Problem

The technology disclosed in the present specification provides a composition for preventing hair loss or promoting hair growth, containing an exosome-like vesicle derived from *ginseng* as an active ingredient.

In an aspect, the exosome-like vesicle may be isolated from *ginseng* root.

In another aspect, the exosome-like vesicle may have a size of from 20 to 500 nm in diameter.

In another aspect, the exosome-like vesicle may be precipitated by ultracentrifugation of extracellular fluid of *ginseng* at 100,000×g or more.

In another aspect, the exosome-like vesicle may have a buoyant density of from 1.00 to 1.20 g/ml in iodixanol.

In another aspect, the active ingredient may activate dermal papilla cells (DPCs) to induce hair growth.

In addition, the technology disclosed in the present specification provides a method for preparing the composition, including (1) obtaining a juice by squeezing *ginseng*; (2) centrifuging the juice to remove residues and obtain a supernatant; and (3) ultracentrifuging the supernatant to obtain an exosome-like vesicle.

In an aspect, the centrifugation in the step (2) may be conducted at from 500 to 3,000×g for from 10 to 30 minutes.

In another aspect, the ultracentrifugation in the step (3) may be conducted using sucrose cushion density gradient and iodixanol density gradient.

In another aspect, the ultracentrifugation in the step (3) may be conducted at from 100,000 to 200,000×g for from 2 to 6 hours.

In another aspect, the exosome-like vesicle in the step (3) may be obtained by ultracentrifuging a supernatant and then isolating a fraction having a buoyant density of from 1.00 to 1.20 g/ml in iodixanol.

Advantageous Effects of Invention

In an aspect, the technology disclosed in the present specification has an effect of providing a composition for preventing hair loss or promoting hair growth, containing an exosome-like vesicle, which is a complex physiologically active substance extracted from *ginseng*, as an active ingredient.

The composition has an effect of protecting and preventing a phenomenon that the hair falls off from the scalp or a phenomenon that the hair is thinned or tapered.

The composition has an effect of realizing not only a hair growth function to produce new hair or a function to promote the hair growth but also a function to promote the delay from the anagen phase to the catagen phase in the hair growth cycle and a function to allow the existing hair to grow healthy.

In another aspect, the technology disclosed in the present specification has an effect of providing a method for preparing the composition.

DESCRIPTION OF EMBODIMENTS

Figure 1:
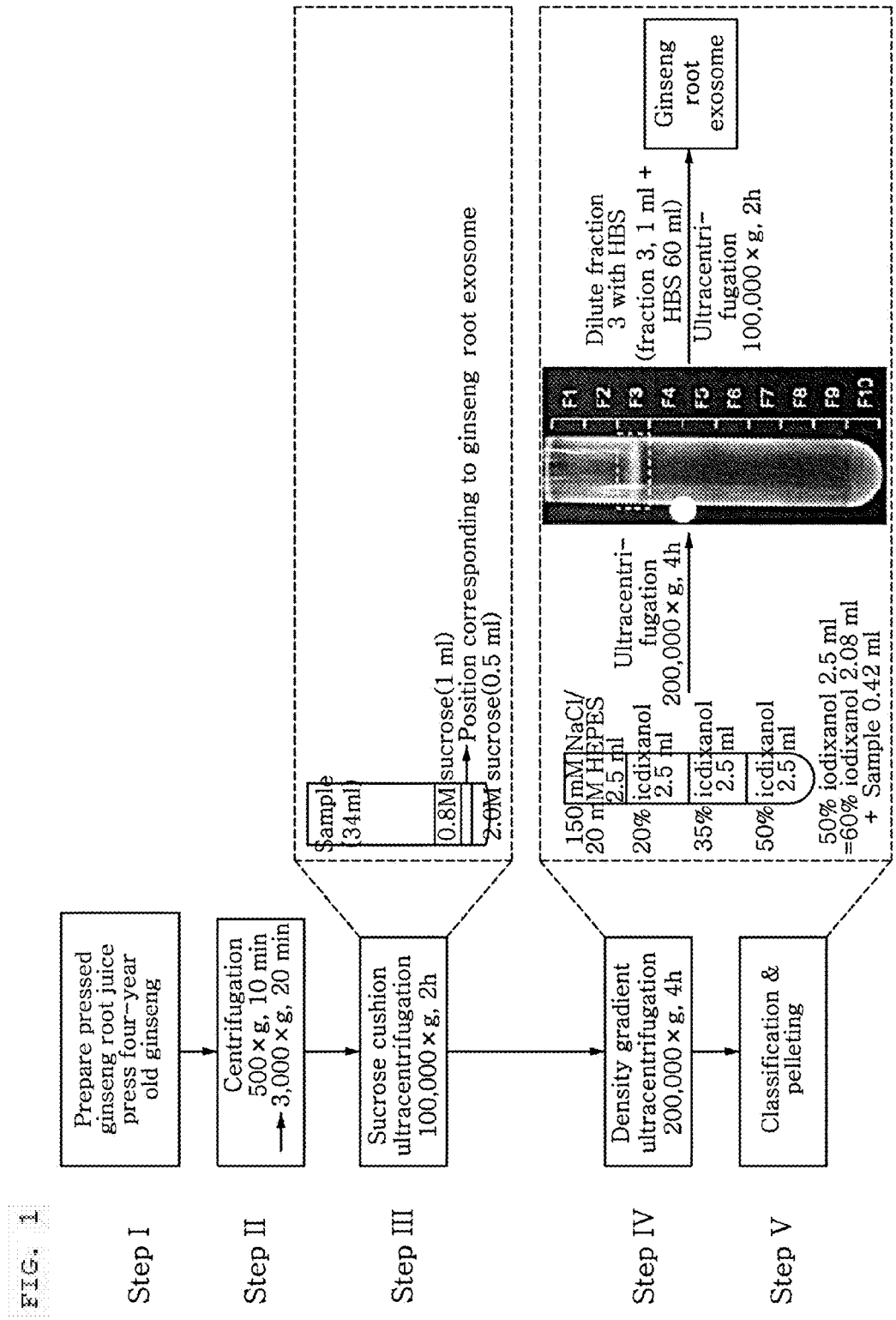
FIG. 1 illustrates a stepwise process of isolating exosome-like vesicles from a juice of *ginseng* root according to Example of the present specification.

Hereinafter, the present invention will be described in detail.

The present specification provides a composition for preventing hair loss or promoting hair growth which contains an exosome-like vesicle derived from *ginseng* as an active ingredient. The present specification provides a composition for preventing hair loss or promoting hair growth which contains exosome-like vesicles derived from *ginseng*, which is not an extract derived from *ginseng*, and specifically exosome-like vesicles derived from extracellular fluid of *ginseng* as an active ingredient.

The hair growth cycle may be divided into three main stages known as the anagen phase, the catagen phase, and the telogen phase. During the anagen phase, hair growth takes place as hair follicles grow deep into the skin with rapid cell proliferation. The next phenomenon is the catagen phase of a transitional period in which the breakdown of the cell division is prominent, and during this process, the hair follicles gradually regress and hair growth stops. In the telogen phase of the next phenomenon, the regressed hair follicles include germs having densely packed dermal papilla cells. The onset of a new anagen phase from the telogen phase is induced by rapid cell proliferation in germs, swelling of the dermal papilla, and synthesis of basement membrane constituents. In general, "hair growth" takes place in the anagen phase and is promoted by the induction from the telogen phase to the anagen phase and the delay from the anagen phase to the catagen phase.

In the present specification, the term "hair loss" refers to a phenomenon that the hair falls off from the scalp or a phenomenon that hair is thinned or tapered, the term "prevention of hair loss" refers to prevention and suppression of the hair loss phenomenon as described above, and the term "promotion of hair growth" refers to not only a hair growth function to produce new hair or a function to promote the hair growth but also a function to promote the delay from the anagen phase to the catagen phase and a function to allow the existing hair to grow healthy.

In an exemplary embodiment, the *ginseng* may be one or more selected from the group consisting of seeds, roots, stems, leaves, and fruits of *Panax* species plants, specific *Panax* species plants include *Panax ginseng, Panax quinquefolium, Panax notoginseng, Panax japonicum, Panax trifolium, Panax pseudoginseng*, or *Panax vietnamensis*, and it is possible to use red *ginseng*, fresh *ginseng*, white *ginseng*, cultivated *ginseng*, cultivated wild *ginseng*, or wild *ginseng* including wild cultivated *ginseng* and wild *ginseng* culture byproducts classified depending on the processing conditions and growth environments without limitation in varieties or kinds.

In the present specification, the term "exosome-like vesicle" refers to nano-sized extracellular vesicle secreted from cells and released into the extracellular space, namely, an extracellular vesicle, and the vesicle includes exosomes and is used in the broadest concept, including an vesicle similar in a nanosized vesicular structure and a composition with the exosome. The exosome-like vesicles are membrane-structured vesicles, the inner part and the outer part are distinguished from each other, and the exosome-like vesicles have cell membrane lipids, membrane proteins, genetic materials, and cytoplasmic components of cells so as to allow to indirectly understand the nature and state of the cell. In addition, the exosome-like vesicles bind to other cells and tissues to transport membrane constituents, mRNAs, miRNAs, proteins (growth hormone, cytokine, and the like) and act as extracellular transporters which mediate cell-cell interactions by transporting these transmitter substances to the recipient cells.

In the present specification, the term "exosome-like vesicle derived from *ginseng*" refers to a nano-sized exosome-like vesicle secreted from *ginseng* cells. The exosomelike vesicles may be isolated from the extracellular fluid of *ginseng*, and the isolated exosome-like vesicles may be physically isolated from the tissue or cells originally present in whole or in part.

In an exemplary embodiment, the exosome-like vesicle may be isolated from *ginseng* root.

In an aspect, the exosome-like vesicle may be an extracellular vesicle having a diameter of from 20 to 500 nm. In another aspect, the exosome-like vesicle may be an extracellular vesicle having a diameter of 20 nm or larger, 30 nm or larger, 40 nm or larger, 50 nm or larger, 60 nm or larger, 70 nm or larger, 80 nm or larger, 90 nm or larger, 100 nm or larger and 500 nm or smaller, 450 nm or smaller, 400 nm or smaller, 350 nm or smaller, 300 nm or smaller, 250 nm or smaller, 200 nm or smaller, 150 nm or 100 nm or smaller.

In another aspect, the exosome-like vesicle may be precipitated by ultracentrifugation of extracellular fluid of *ginseng* at 100,000×g or more, specifically from 100,000 to 200,000×g, at or 100,000×g.

In another aspect, the exosome-like vesicle may have a buoyant density of from 1.00 to 1.20 g/ml, from 1.03 to 1.20 g/ml, or from 1.06 to 1.20 g/ml in iodixanol. The buoyant density refers to the density measured by a density gradient centrifugation method.

In another aspect, the exosome-like vesicle may have a membrane component which is chemically or physically modified, for example, so as to efficiently conduct the desired function in the target cell. For example, the membrane component of the exosome-like vesicle may be modified by a chemical method using a thiol group (—SH) or an amine group (—NH$_2$) or may be chemically modified by chemically bonding a target inducing substance, a cell membrane fusion substance, and polyethylene glycol to the exosome-like vesicle.

In an exemplary embodiment, the exosome-like vesicle may be isolated by using one or more methods selected from the group consisting of ultracentrifugation, differential centrifugation, equilibrium density centrifugation, density gradient, filtration, dialysis, and free-flow electrophoresis, but the method of isolating the exosome-like vesicle is not limited thereto.

Density gradient is the most commonly used method to distinguish materials having different densities, and the exosome-like vesicle according to the present specification may be isolated through density gradient since the exosome-like vesicle has a distinguishable density. Specific examples of the method may be conducted using a density gradient isolating material such as ficoll, glycerol, sucrose, cesium chloride, or iodixanol, but the method is not limited thereto. In an aspect, the density gradient may be used together with ultracentrifugation and the like. In another aspect, gel filtration or ultrafiltration may be used to screen for the exosome-like vesicles. In still another aspect, dialysis may be used instead of filtration to remove small molecules. In yet another aspect, free-flow electrophoresis may be used.

In an exemplary embodiment, the *ginseng*-derived exosome-like vesicle may be obtained by (1) obtaining a juice containing extracellular fluid of *ginseng* from *ginseng*; (2) centrifuging the juice to remove residues and obtain a supernatant; and (3) ultracentrifuging the supernatant to obtain an exosome-like vesicle.

In an exemplary embodiment, the juice in the step (1) is a liquid squeezed out from *ginseng* and may be obtained by appropriately using methods such as mechanical decomposition and treatment with a chemical substance. In an aspect, the juice may be obtained by pressing *ginseng*, and the pressing process may be suitably selected and carried out by those skilled in the art according to the methods known in the art.

In an exemplary embodiment, the centrifugation in the step (2) may be conducted at from 500 to 3,000×g for from 10 to 30 minutes. At this time, the centrifugation may be conducted stepwise by changing the speed or time.

In an exemplary embodiment, the ultracentrifugation in the step (3) may be ultracentrifugation using sucrose cushion density gradient and iodixanol density gradient.

In an exemplary embodiment, the ultracentrifugation in the step (3) may be conducted at from 100,000 to 200,000×g for from 2 to 6 hours. At this time, the ultracentrifugation may be conducted stepwise by changing the speed or time.

In an exemplary embodiment, the ultracentrifugation in the step (3) may be conducted through a series of ultracentrifugation processes including ultracentrifugation at from 100,000 to 200,000×g for from 2 to 6 hours using sucrose cushion density gradient and ultracentrifugation using iodixanol density gradient.

In an exemplary embodiment, the exosome-like vesicle in the step (3) may be obtained by isolating the fraction which is obtained by ultracentrifuging and then fractionating the supernatant and has a buoyant density of from 1.00 to 1.20 g/ml. At this time, the isolated fraction may be further diluted with a buffer solution and ultracentrifuged, and specifically, the isolated fraction may be ultracentrifuged at 100,000×g for 2 hours to isolate pelleted exosome-like vesicles having a diameter of from 20 to 500 nm.

In another aspect, the present specification provides a method of preventing hair loss or promoting hair growth which includes administering an exosome-like vesicle derived from *ginseng* to a subject in need thereof in an effective amount to prevent hair loss or to promote hair growth.

In another aspect, the present specification provides *ginseng*-derived exosome-like vesicles for preventing hair loss or promoting hair growth of a subject.

In another aspect, the present specification provides use of *ginseng*-derived exosome-like vesicles for preparing a *ginseng*-derived exosome-like vesicle-containing composition for preventing hair loss or promoting hair growth of a subject.

In an exemplary embodiment, the *ginseng*-derived exosome-like vesicle may be applied or administered to a subject in the form of a pharmaceutical composition, a cosmetic composition, or a food composition.

In an exemplary embodiment, the *ginseng*-derived exosome-like vesicle may be applied or administered to the skin or scalp of a subject.

In an exemplary embodiment, the composition may be a lyophilized formulation. The composition may be a lyophilized formulation in a ready-to-use sealed package or a packaging container.

The present specification also provides a hair loss preventing kit or hair growth promoting kit including a composition which contains an exosome-like vesicle derived from *ginseng* as an active ingredient and has a lyophilized formulation; and sterilized water or purified water. The kit may be a kit in a ready-to-use sealed package or a packaging container.

According to an exemplary embodiment, the composition may be a pharmaceutical composition.

The pharmaceutical composition may additionally contain preservatives, stabilizers, wetting agents or emulsifying accelerators, pharmaceutical adjuvants such as salts and/or buffers for controlling osmotic pressure, and other therapeutically useful substances in addition to the *ginseng*-derived exosome-like vesicles. The pharmaceutical composition may be formulated into various forms of oral or parenteral administration agents according to conventional methods.

Examples of the oral administration agent may include tablets, pills, hard and soft capsules, liquids, suspensions, emulsions, syrups, powders, powder remedy, infinitesimal grains, granules, and pellets, and these formulations may contain surfactants, diluents (for example, lactose, dextrose, sucrose, mannitol, sorbitol, cellulose, and glycine) and lubricants (for example, silica, talc, stearic acid and its magnesium or calcium salt, and polyethylene glycol) in addition to the active ingredient. The tablets may also contain binders such as magnesium aluminum silicate, starch paste, gelatin, tragacanth, methylcellulose, sodium carboxymethylcellulose, and polyvinylpyrrolidine, and the tablets may optionally contain pharmaceutical additives such as starch, agar, disintegrants such as alginic acid or its sodium salt, absorbents, colorants, flavors, and sweeteners. The tablets may be prepared by conventional mixing, granulating, or coating methods.

In addition, the formulation in a parenteral administration form may be a formulation in a transdermal administration form, and for example, the formulation may be a formulation such as an injection, a drop, an ointment, a lotion, a gel, a cream, a spray, a suspension, an oil, a suppository, or a patch, but it is not limited thereto.

The dosage of the active ingredient is within the level of those skilled in the art, and the daily dosage of the drug depends on various factors such as the progression of disease, time of onset, age, state of health, and complications of the subject to be administered, but the composition may be administered in an amount of from 1 μg/kg to 200 mg/kg in an aspect and from 50 μg/kg to 50 mg/kg in another aspect per one day by dividing into one to three times, and the dosage does not limit the scope of the present invention in any way.

The pharmaceutical composition may be an external preparation for skin, and the external preparation for skin may be a generic term including any preparation to be applied at the outside of the skin and may include various formulations of medicaments.

According to an exemplary embodiment, the composition may be a cosmetic composition.

The cosmetic composition may additionally contain functional additives and components to be contained in general cosmetic compositions in addition to the *ginseng*-derived exosome-like vesicles. The functional additives may include components selected from the group consisting of water-soluble vitamins, oil-soluble vitamins, polymeric peptides, polymeric polysaccharides, sphingolipids, and seaweed extracts. Components to be blended into the cosmetic composition other than these may include oil and fat components, moisturizers, emollients, surfactants, organic or inorganic pigments, organic powders, ultraviolet absorbers, preservatives, bactericides, antioxidants, plant extracts, pH adjusting agents, alcohols, coloring matters, fragrances, blood circulation accelerators, cold reserving agents, antiperspirants, purified water, and the like.

The formulation of the cosmetic composition is not particularly limited and may be appropriately selected depending on the purpose. For example, the cosmetic composition may be prepared in one or more formulations selected from the group consisting of skin lotions, skin softeners, skin toners, astringents, lotions, milky lotions, moisturizing lotions, nourishing lotions, massage creams, nourishing creams, moisturizing creams, hand creams, foundations, essences, nourishing essences, packs, soaps, cleansing foams, cleansing lotions, cleansing creams, body lotions, and body cleansers, but the formulation is not limited thereto.

In a case in which the formulation of the present invention is a paste, a cream, or a gel, animal fibers, plant fibers, wax, paraffin, starch, tragacanth, cellulose derivatives, polyethylene glycol, silicone, bentonite, silica, talc, zinc oxide, or the like may be used as a carrier component.

In a case in which the formulation of the present invention is a powder or a spray, lactose, talc, silica, aluminum hydroxide, calcium silicate, or polyamide powder may be used as a carrier component, and particularly in a case in which the formulation is a spray, the formulation may additionally contain a propellant such as chlorofluorohydrocarbons, propane/butane, or dimethyl ether.

In a case in which the formulation of the present invention is a solution or an emulsion, a solvent, a solvating agent, or an emulsifier is used as a carrier component, and examples thereof may include water, ethanol, isopropanol, ethyl carbonate, ethyl acetate, benzyl alcohol, benzyl benzoate, propylene glycol, 1,3-butyl glycol oil, glycerol aliphatic acid esters, fatty acid esters of polyethylene glycol or sorbitan.

In a case in which the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, tracant, or the like may be used as a carrier component.

In a case in which the formulation of the present invention is a surfactant-containing cleansing, aliphatic alcohol sulfates, aliphatic alcohol ether sulfates, sulfosuccinic acid monoesters, isethionates, imidazolinium derivatives, methyl taurate, sarcosinates, fatty acid amide ether sulfates, alkylamidobetaines, aliphatic alcohols, fatty acid glycerides, fatty acid diethanolamides, vegetable oils, linolenic derivatives, ethoxylated glycerol fatty acid esters, or the like may be used as a carrier component.

According to an exemplary embodiment, the composition may be a food composition.

The food composition may be a formulation in the form of a liquid or a solid, examples of the food composition may include various foods, beverages, gums, tea, vitamin complexes, and health supplement foods, and the food composition may be used in the form of powders, granules, tablets, capsules, or beverages. Components to be commonly used in the field may be selected and blended into the food composition of each formulation in addition to the active ingredient by those skilled in the art without difficulty depending on the formulation or the purpose of use, and a synergistic effect may be obtained in a case in which the active ingredient is simultaneously applied with other raw materials.

There are no particular limitation on the liquid components which may be contained in the food composition in addition to the active ingredient disclosed in the present specification, and various flavors or natural carbohydrates may be added as an additional component as in ordinary beverages. Examples of the natural carbohydrate may include monosaccharides, disaccharides such as glucose and fructose, polysaccharides such as maltose and sucrose, common saccharides such as dextrin and cyclodextrin, and sugar alcohols such as xylitol, sorbitol, and erythritol. As the flavors, natural flavors (tau martin, *stevia* extracts (for example, rebaudioside A and glycyrrhizin) and synthetic flavors (for example, saccharin and aspartame) may be advantageously used. The ratio of the natural carbohydrate may be generally about from 1 to 20 g and, in an aspect, about from 5 to 12 g per 100 ml of the composition disclosed in the present specification.

In an aspect, the food composition may contain various nutrients, vitamins, minerals (electrolytes), flavors such as synthetic flavors and natural flavors, colorants and thickeners (cheese, chocolate, and the like), pectic acid and its salts, alginic acid and its salts, organic acids, protective colloid thickeners, pH adjusting agents, stabilizers, preservatives, glycerin, alcohols, and carbonating agents used in carbonated beverages. In another aspect, the food composition may contain pulp for the production of natural fruit juices and vegetable beverages. These components may be used independently or in combination. The ratio of the additives may vary, but it is generally selected in a range of from 0.001 to about 20 parts by weight per 100 parts by weight of the composition disclosed in the present specification.

EMBODIMENTS

Hereinafter, the present invention will be described in more detail with reference to Examples. It should be apparent to those skilled in the art that these Examples are for illustrative purposes only and that the scope of the present invention is not construed as being limited by these Examples.

Example 1. Isolation of *Ginseng*-Derived Exosome-Like Vesicles (Step 1) First, 4-year old *ginseng* root was prepared and pressed to prepare a juice containing extracellular fluid of *ginseng* root.

(Step 2) The juice was centrifuged at 4° C. and 500×g for 10 minutes to obtain a supernatant and the supernatant was centrifuged again at 4° C. and 3,000×g for 20 minutes to obtain a supernatant.

(Step 3) To a 35 ml ultracentrifuge tube, 0.5 ml of 2.0 M sucrose, 1 ml of 0.8 M sucrose, and 32 ml of the supernatant from which foreign substances had been removed were added in this order and ultracentrifuged at 4° C. and 100,000×g for 2 hours. After the ultracentrifugation, *ginseng* root exosome-like vesicles were positioned between the 2.0 M sucrose layer and the 0.8 M sucrose layer by the density. Thereafter, the solution was removed from the top of the tube to isolate the layer containing *ginseng* root exosome-like vesicles.

(Step 4) The layer containing the *ginseng* root exosome-like vesicles thus isolated was subjected to density gradient ultracentrifugation. Specifically, 0.42 ml of the layer containing the *ginseng* root exosome-like vesicles thus isolated and 2.08 ml of 60% iodixanol were mixed to finally prepare 2.5 ml of 50% iodixanol, the 2.5 ml of 50% iodixanol was placed in a 12 ml ultracentrifuge tube, 2.5 ml of 35% iodixanol, 2.5 ml of 20% iodixanol, and 2.5 ml of 150 mM NaCl/20 mM HEPES were successively placed thereon, and ultracentrifugation was conducted at 4° C. and 200,000×g for 4 hours. Thereafter, a fraction was obtained from the top of the tube in an amount of 1 ml and the density thereof was measured to obtain Fraction 3 (1.08 g/ml) corresponding to the density of exosome-like vesicles (see FIG. 1).

(Step 5) Fraction 3 thus obtained was diluted with 60 ml of HBS (HEPES-buffered saline), placed in a ultracentrifuge tube having a capacity of 70 ml, and ultracentrifuged at 4° C. and 100,000×g for 2 hours to obtain pelleted *ginseng*-derived exosome-like vesicles.

Test Example 1. Transmission Electron Microscopic Analysis of *Ginseng*-Derived Exosome-Like Vesicles The size and shape of the *ginseng*-derived exosome-like vesicles obtained in Example 1 were analyzed using a transmission electron microscope (TEM).

Figure 2:
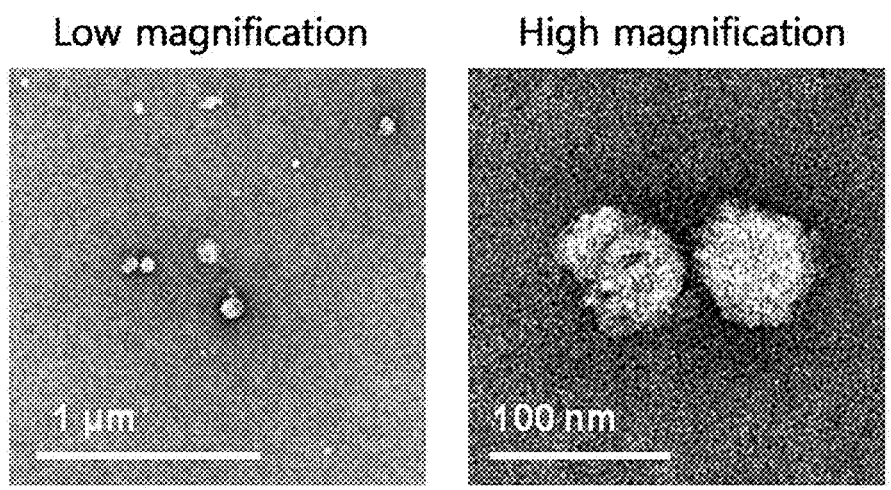
FIG. 2 illustrates images of *ginseng*-derived exosome-like vesicles according to Test Example of the present specification taken using a transmission electron microscope.

FIG. 2 illustrates images of *ginseng*-derived exosome-like vesicles taken using a transmission electron microscope, and it has been confirmed that *ginseng*-derived exosome-like vesicles have a diameter of from 50 to 100 nm and are generally spherical.

Test Example 2. Hair Follicular Cells Proliferation Effect

Primary human dermal papilla cells (hDPC) were treated with the *ginseng* root-extracted exosome-like vesicles isolated in Example 1 at various concentrations and the effect of *ginseng*-derived exosome-like vesicles on the hair follicular cell proliferation was examined.

Specifically, hDPCs (passage 6, 7) were cultured in a 96-well plate at $2 \times 10^4$ cells/well for 24 hours (5% $CO_2$, 37° C.) and treated with the *ginseng*-derived exosome-like vesicles at various concentrations (0.1 to 100 μg/ml). Thereafter, the hDPCs thus treated were cultured for 48 hours, the culture medium was changed, and the proliferation effect was then evaluated through MTT assay (100 μg/well, measurement of absorbance at 570 nm).

Figure 3:
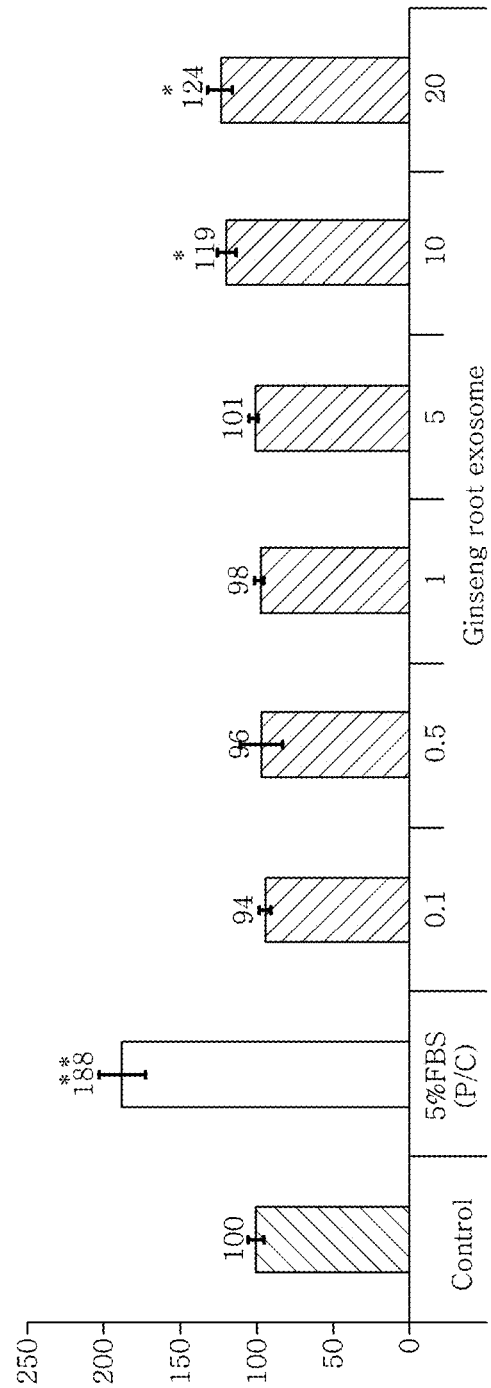
FIG. 3 illustrates the results on hair follicular cell proliferation when primary human dermal papilla cells are treated with *ginseng*-derived exosome-like vesicles in a low concentration range (0.1 to 20 μg/ml) in Test Example of the present specification.
Figure 4:
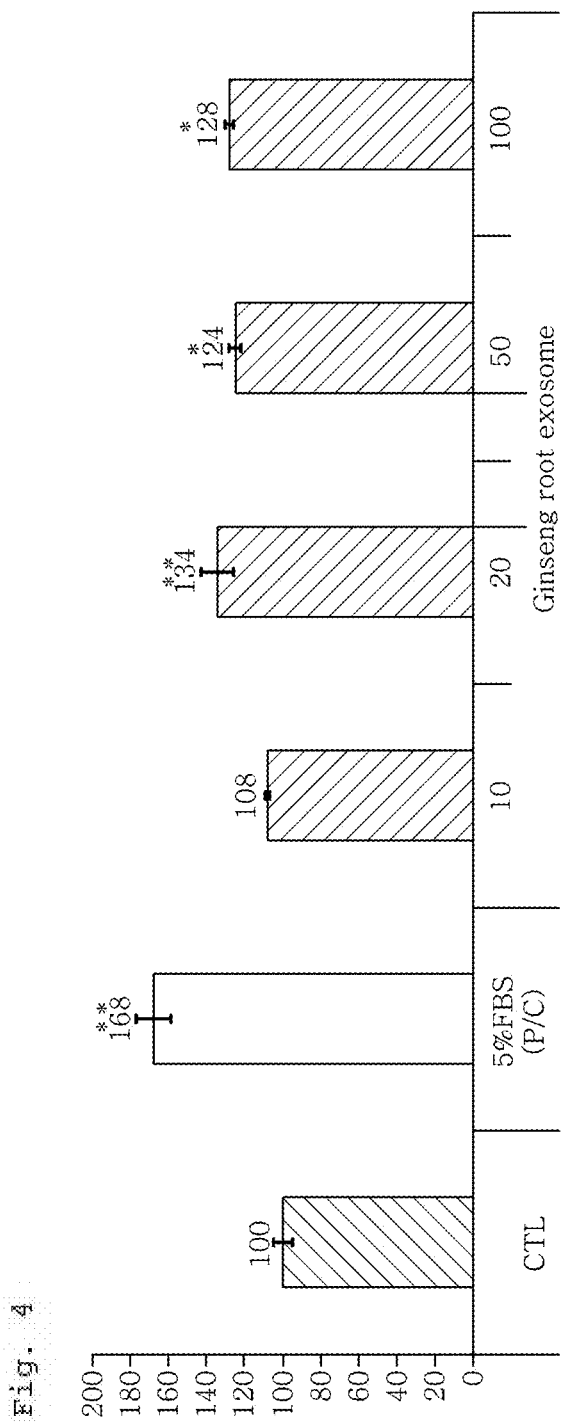
FIG. 4 illustrates the results on hair follicular cell proliferation when primary human dermal papilla cells are treated with *ginseng*-derived exosome-like vesicles in a high concentration range (10 to 100 μg/ml) in Test Example of the present specification.

FIG. 3 illustrates the results on hair follicular cell proliferation when primary human dermal papilla cells are treated with the exosome-like vesicles in a low concentration range (0.1 to 20 μg/ml), and FIG. 4 illustrates the results on hair follicular cell proliferation when primary human dermal papilla cells are treated with the exosome-like vesicles in a high concentration range (10 to 100 μg/ml). In FIGS. 3 and 4, the vertical axis represents the results on hair follicular cell proliferation (% with respect to control (CTL)) and 5% FBS positive control was used for comparison. As a result, it has been found that an effect of proliferating hair follicular cells is obtained when primary human dermal papilla cells are treated with *ginseng*-derived exosome-like vesicles.

Test Example 3. Hair Shaft Elongation Effect

A hair follicle organ culture was treated with the *ginseng* root-extracted exosome-like vesicles isolated in Example 1 at various concentrations and the effect of *ginseng*-derived exosome-like vesicles on the hair shaft elongation was examined.

Specifically, hair follicle organs were isolated one by one from the scalp tissues in the occipital region of 43-year-old and 63-year-old male subjects and cultured in William's E medium (L-glutamine (2 mM), insulin (10 μg/ml), hydrocortisone (10 ng/ml), an antibiotic (1%), and an antifungal agent (1%)). The hair follicle tissue which had grown but was not treated with the drug was taken as a control, and a group treated with 50 μM MNX (minoxidil) and a group treated with 20 ppm of *ginseng* main ingredient were taken as a positive control. The experimental group was treated with 10 μg/ml of the *ginseng* root-extracted exosome-like vesicles isolated in Example 1. In 3 and 7 days after the treatment, the length was measured and the photograph was taken, respectively.

Figure 5:
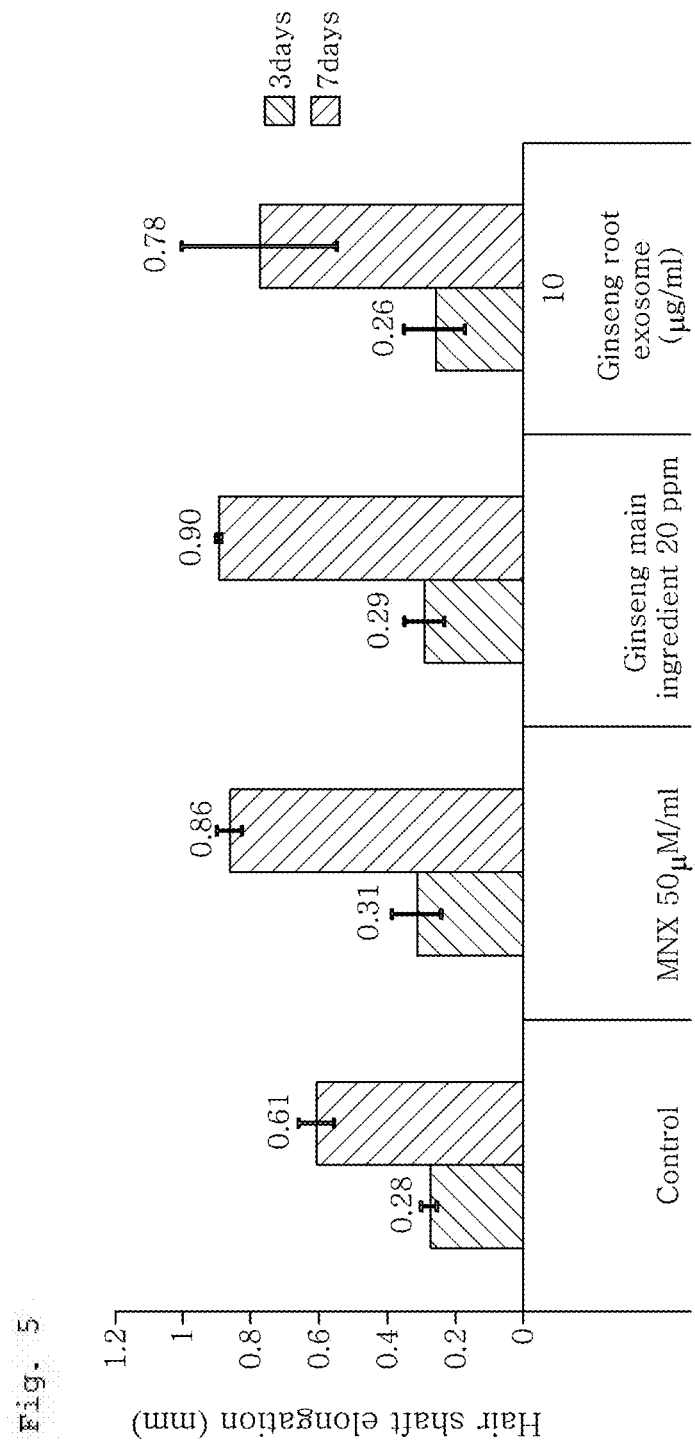
FIG. 5 is a graph illustrating the hair shaft elongation effect when a hair follicle organ culture is treated with *ginseng*-derived exosome-like vesicles in Test Example of the present specification.
Figure 6:
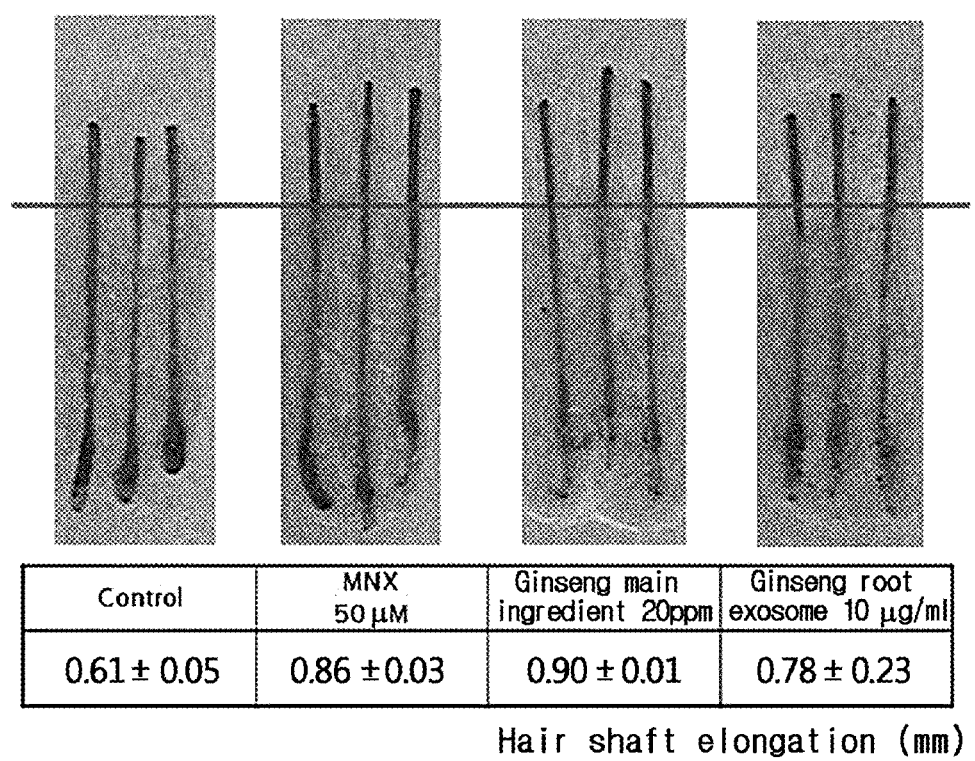
FIG. 6 is a photograph illustrating the hair shaft elongation effect when a hair follicle organ culture is treated with *ginseng*-derived exosome-like vesicles in Test Example of the present specification.

FIGS. 5 and 6 illustrate the results on hair shaft elongation when a hair follicle organ culture is treated with 10 μg/ml of the exosome-like vesicles. As a result, it has been found that

*ginseng*-derived exosome-like vesicles have a hair shaft elongation effect since hair shaft elongation was observed as compared to the control when a hair follicle organ culture is treated with 10 μg/ml of the exosome-like vesicles.

Formulation Examples of compositions according to an aspect of the present specification are described below, but are applicable to various other formulations, and are intended to be illustrative only but not to limit the present invention.

[Formulation Example 1] Soft Capsule 50 mg of *ginseng*-derived exosome-like vesicles of Example 1, 80 to 140 mg of L-carnitine, 180 mg of soybean oil, 2 mg of palm oil, 8 mg of hardened vegetable oil, 4 mg of yellow pear, and 6 mg of lecithin were mixed, and the mixture was filled by 400 mg per one capsule according to a conventional method to prepare a soft capsule.

[Formulation Example 2] Tablet 50 mg of *ginseng*-derived exosome-like vesicles of Example 1, 200 mg of galactooligosaccharide, 60 mg of lactose, and 140 mg of maltose were mixed, the mixture was granulated using a fluidized bed dryer, 6 mg of sugar ester was added to the granules, and the mixture was then tableted using a tablet machine to prepare a tablet.

[Formulation Example 3] Granules 50 mg of *ginseng*-derived exosome-like vesicles of Example 1, 250 mg of anhydrous crystalline glucose, and 550 mg of starch were mixed, the mixture was granulated using a fluidized bed granulator, and the granules were then filled in a bag to prepare granules.

[Formulation Example 4] Drink 50 mg of *ginseng*-derived exosome-like vesicles of Example 1, 10 g of glucose, 0.6 g of citric acid, and 25 g of liquid oligosaccharide were mixed, 300 ml of purified water was added to the mixture, and the mixture thus obtained was filled in each bottle by 200 ml. The mixture filled in the bottle was sterilized at 130° C. for 4 to 5 seconds to prepare a drink beverage.

[Formulation Example 5] Ointment

An ointment was prepared by a conventional method according to the composition presented in Table 1 below.

TABLE 1

| Ingredients | Content (% by weight) |
| --- | --- |
| *Ginseng*-derived exosome-like vesicles of Example 1 | 2.00 |
| Glycerin | 8.00 |
| Butylene glycol | 4.00 |
| Liquid paraffin | 15.00 |
| Beta-glucan | 7.00 |
| Carbomer | 0.10 |
| Caprylic/Capric Triglyceride | 3.00 |
| Squalane | 1.00 |
| Cetearyl glucoside | 1.50 |

TABLE 1-continued

| Ingredients | Content (% by weight) |
| --- | --- |
| Sorbitan stearate | 0.40 |
| Cetearyl alcohol | 1.00 |
| Bees wax | 4.00 |
| Purified water | Balance |
| Total | 100.00 |

[Formulation Example 6] Cosmetic Liquid Preparation

A cosmetic liquid preparation was prepared by a conventional method according to the composition presented in Table 2 below.

TABLE 2

| Ingredients | Content (% by weight) |
| --- | --- |
| *Ginseng*-derived exosome-like vesicles of Example 1 | 2.00 |
| Hydroxyethylene cellulose (2% aqueous solution) | 12.00 |
| Xanthan gum (2% aqueous solution) | 2.00 |
| 1,3-Butylene glycol | 6.00 |
| Concentrated glycerin | 4.00 |
| Sodium hyaluronate (1% aqueous solution) | 5.00 |
| Purified water | Balance |
| Total | 100.00 |

[Formulation Example 7] Shampoo

A shampoo was prepared by a conventional method according to the composition presented in Table 3 below.

TABLE 3

| Ingredients | Content (% by weight) |
| --- | --- |
| *Ginseng*-derived exosome-like vesicles of Example 1 | 2.00 |
| Sodium lauryl sulfate | 10.00 |
| Cocamidopropyl betaine | 3.00 |
| Carboxyl vinyl polymer | 0.30 |
| Polyquaternium-10 | 0.20 |
| Cetyltrimethylammonium chloride | 0.10 |
| Purified water | Balance |
| Total | 100.00 |

[Formulation Example 8] Rinse

A rinse was prepared by a conventional method according to the composition presented in Table 4 below.

TABLE 4

| Ingredients | Content (% by weight) |
| --- | --- |
| *Ginseng*-derived exosome-like vesicles of Example 1 | 2.00 |
| Cetyl alcohol | 2.00 |
| Stearyl alcohol | 2.50 |
| Behenyl alcohol | 0.50 |
| Silicone emulsion | 0.40 |

TABLE 4-continued

| Ingredients | Content (% by weight) |
|---|---|
| Cyclomethicone | 1.00 |
| Dimethyldistearylammonium chloride | 0.10 |
| Purified water | Balance |
| Total | 100.00 |

While specific parts of the present invention have been described in detail, those skilled in the art will appreciate that these specific descriptions are merely preferred embodiments and that the scope of the present invention is not limited thereby. Accordingly, the actual scope of the present invention will be defined by the appended claims and their equivalents.

We claim:

1. A method for preventing hair loss or promoting hair growth, comprising administering an effective amount of an isolated exosome-like vesicle derived from extracellular fluid of *ginseng* for preventing hair loss or promoting hair growth to a subject in need thereof, wherein the method prevents hair loss or promotes hair growth.

2. The method for preventing hair loss or promoting hair growth according to claim 1, wherein the exosome-like vesicle is isolated from *ginseng* root.

3. The method for preventing hair loss or promoting hair growth according to claim 1, wherein the exosome-like vesicle has a diameter of 20 to 500 nm.

4. The method for preventing hair loss or promoting hair growth according to claim 1, wherein the exosome-like vesicle is precipitated by ultracentrifugation of extracellular fluid of *ginseng* at 100,000×g or more.

5. The method for preventing hair loss or promoting hair growth according to claim 1, wherein the exosome-like vesicle has a buoyant density of 1.00 to 1.20 g/ml in iodixanol.

6. The method for preventing hair loss or promoting hair growth according to claim 1, wherein the exosome-like vesicle activates dermal papilla cells (DPCs) to induce hair growth.

* * * * *